(12) United States Patent
Brooke

(10) Patent No.: US 8,801,864 B2
(45) Date of Patent: Aug. 12, 2014

(54) CLEANING COMPOSITIONS

(75) Inventor: Anthony Brooke, Selby (GB)

(73) Assignee: Cleveland Biotech Limited, Stockton on Tees (GB)

( * ) Notice: Subject to any disclaimer, the term of this patent is extended or adjusted under 35 U.S.C. 154(b) by 0 days.

(21) Appl. No.: 13/825,927

(22) PCT Filed: Sep. 30, 2011

(86) PCT No.: PCT/GB2011/001422
§ 371 (c)(1),
(2), (4) Date: Mar. 25, 2013

(87) PCT Pub. No.: WO2012/042220
PCT Pub. Date: Apr. 5, 2012

(65) Prior Publication Data
US 2013/0184196 A1  Jul. 18, 2013

(30) Foreign Application Priority Data

Oct. 1, 2010  (GB) .................................. 1016502.5

(51) Int. Cl.
*C11D 3/38* (2006.01)
*C11D 1/00* (2006.01)
*C11D 1/83* (2006.01)
*B08B 3/04* (2006.01)

(52) U.S. Cl.
USPC ............. 134/25.2; 134/25.3; 134/39; 134/42; 510/101; 510/199; 510/238; 510/392; 510/421; 510/426; 510/434; 510/462; 510/463; 510/488; 424/93.4; 424/93.46; 424/93.462; 422/28; 435/252.5; 435/264

(58) Field of Classification Search
USPC ......... 510/101, 199, 238, 392, 421, 426, 434, 510/462, 463, 488; 424/93.4, 93.46, 424/93.462; 422/28; 435/252.5, 264; 134/25.2, 25.3, 39, 42
See application file for complete search history.

(56) References Cited

U.S. PATENT DOCUMENTS

| | | | |
|---|---|---|---|
| 5,863,882 A | 1/1999 | Lin et al. | |
| 6,165,965 A | 12/2000 | Schalitz et al. | |
| 2002/0182184 A1 | 12/2002 | Pearl et al. | |
| 2005/0164902 A1* | 7/2005 | Man et al. | 510/503 |
| 2010/0279388 A1 | 11/2010 | Sakamoto et al. | |

FOREIGN PATENT DOCUMENTS

| | | |
|---|---|---|
| CA | 2198327 A1 | 8/1998 |
| DE | 4012380 A1 | 10/1991 |
| EP | 1 967 578 A1 | 9/2008 |
| WO | 03002704 A1 | 1/2003 |
| WO | 2006125283 A1 | 11/2006 |
| WO | 2009/043709 A1 | 4/2009 |
| WO | 2010/130541 A1 | 11/2010 |

* cited by examiner

Primary Examiner — Brian P Mruk
(74) Attorney, Agent, or Firm — Larson & Anderson, LLC

(57) ABSTRACT

An aqueous composition is disclosed, comprising at least one strain of Class 1 *Bacillus* bacterial spores, selected from *Bacillus Cirulans, Bacillus Megaterium, Bacillus Licheniformis, Bacillus Pumilus, Bacillus Sphaericus, Bacillus Subtilis* sub species 10144 and *Bacillus Subtilis* sub species 8646, a terpene and one or more surfactants. The terpene is preferably d-limonene. A method for cleaning surfaces is also disclosed, which method comprises deploying an aqueous composition comprising at least one strain of Class 1 *Bacillus* bacterial spores, selected from *Bacillus Cirulans, Bacillus Megaterium, Bacillus Lichenforms, Bacillus Pumilus, Bacillus Sphaericus, Bacillus Subtilis* sub species 10144 and *Bacillus Subtilis* sub species 8646, a terpene and one or more surfactants to a surface.

18 Claims, 6 Drawing Sheets

| TIME (DAY) | CONTROL | PROBIO | EFFECTIVENESS |
|---|---|---|---|
| 0 | $8.25 \times 10^4$ | $5.9 \times 10^4$ | N/A |
| 2 | $8 \times 10^9$ | $4.65 \times 10^7$ | 172.04 |
| 4 | $1.45 \times 10^9$ | $1.4 \times 10^7$ | 103.57 |
| 6 | $1.15 \times 10^9$ | $1.5 \times 10^7$ | 76.67 |
| 8 | $1.3 \times 10^8$ | $3.3 \times 10^7$ | 3.94 |

Fig. 4

| TIME (HOURS) | PROBIOTIC v ANTIBACTERIAL INHIBITS GROWTH OF BACTERIA (TIMES) |
|---|---|
| 0 | |
| 2 | 3.91 |
| 4 | 4.49 |
| 6 | 11.67 |
| 8 | 22.00 |
| 24 | 13200.00 |

Fig.5

CLEANING COMPOSITIONS

CROSS REFERENCE TO RELATED APPLICATIONS

This application is the US national stage application of PCT/GB2011/001422 filed on Sep. 30, 2011, which claims priority to GB 10 165 02.5 filed Oct. 1, 2010, all of which are incorporated herein by reference for all purposes.

BACKGROUND OF THE INVENTION

1. Field of the Invention

The present invention relates to aqueous cleaning compositions and methods of cleaning surfaces using aqueous cleaning compositions.

2. Description of the Related Art

All environments used by human beings need to be cleaned. Such environments may be categorised as domestic, public or industrial and may include homes, healthcare centres, schools, leisure centres, restaurants, public buildings, work places and industrial settings. Aqueous cleaning compositions are commercially important products and enjoy a wide field of utility in assisting in the removal of dirt and grime from surfaces within these environments.

A wide range of aqueous cleaning compositions have been developed in the art. Such cleaning compositions have a biocidal activity and aim to kill 99.9% of bacteria present in the domestic, public or industrial environment. Disinfection of a surface in the household therefore leaves an environment almost free of bacteria. As set out in Germicidal and Detergent Sanitising Action of Disinfectants, Official Methods of Analysis of the Association of Official Analytical Chemists, paragraph 960.09 and applicable sections, 15$^{th}$ Edition, 1990, a sanitizer should provide a 99.999% reduction (5-log order reduction) within 30 seconds at room temperature, 25±2° C., against several test organisms.

A problem associated with biocidal cleaning compositions in the prior art is that as soon as a surface has been cleaned, the surface is almost free of bacteria. If a pathogenic bacterium were to land on the clean surface, this pathogenic bacterium would experience no competition and would soon colonise to take up the available space. Human beings therefore aim to be too clean. Further, by cleaning surfaces with a biocidal cleaning composition, this effectively forces pathogenic bacteria to evolve and develop immunity to various antibiotic treatments. These resistant strains are difficult to deal with.

In an article by Andrew A. Pollack entitled "A Rising Hospital Threat", in the New York Times dated 27 Feb. 2010, a Gram-negative drug resistant bacterium, known as *Acinetobacter baumannii*, was discussed. There are no known drugs that have been effective in fighting the Gram-negative bacteria, although there are two older antibiotics that were developed in the 1940s that are currently being used in the battle. Those two are colistin and polymyxin B, but they can cause severe kidney and nerve damage.

Further, a survey based on a one-day snapshot taken on 24 Nov. 2008 at 648 hospitals in 47 states in the United States found that more than 1% of U.S. hospital patients are infected with *Clostridium difficile* (*C. diff*). The Association for Professionals in Infection Control and Epidemiology, a national professional society whose members include doctors, nurses and epidemiologists commissioned the survey. The survey determined that 13 out of every 1,000 hospitalized patients tested positive for *C. diff*.

The survey also reports that use of a bleach solution to clean rooms of infected patients is important in trying to prevent the spread of the disease in the hospital and that proper hand washing is essential. The survey reports that the spores are not always killed by alcohol-based disinfectant gels. Therefore, even when using biocidal compositions, a small number of spores of pathogenic bacteria may remain which would quickly colonise.

There is therefore a need for an alternative composition and method for cleaning surfaces in the domestic, public and industrial environment.

It is known to use bacteria within cleaning products. Bacteria are already used in drain maintenance to avoid fat related drain blockages and maintain the condition of drains. This drain maintenance process involves a natural bio-fluid which is a blend of Hazard Group 1 *Bacillus* spores and bio-degradable surfactants. This biofluid is currently provided by Cleveland Biotech Ltd under the trade name GreaseBeta®. Typical applications include the drains serving pot-wash sinks and rotisserie oven condensate discharge lines.

Bacteria are already used in cleaning products for toilets and urinals, wherein the product is designed to dissolve and prevent build up of organic deposits including uric acid deposits and scale. Such cleaning products include aerobic, spore-forming bacterial strains belonging to the genus *Bacillus*. This product is currently provided by Cleveland Biotech Ltd under the trade name Clearinate®. The product is suitable for use in hospitals, hotels, schools, restaurants, public buildings, offices and nursing homes.

Another example is an existing hydrocarbons degrading product, including selected, naturally occurring Hazard Group 1 micro-organisms to degrade hydrocarbons and surfactants to aid the degradation process. This product is currently provided by Cleveland Biotech Ltd. The product is suitable for degrading petroleum hydrocarbons and can be used in treatment plants receiving effluents from oil refineries. Crude oil can contain in excess of 40% aliphatic compounds varying in size from simple alkanes to long chain molecules such as the C25-C35 alkanes. The greater the chain length and the amount of branching the more resistant the compound is to microbial degradation. The product can degrade such recalcitrant compounds. The product is also suitable for sludge farming and land remediation applications.

Therefore, the use of bacteria as an active ingredient in cleaning compositions is known as exemplified in the above examples.

However, there is still a continuing need for more effective products that can be used in domestic, public and industrial environments such as hospitals, hotels, schools, restaurants, public buildings, offices and nursing homes for cleaning hard or soft surfaces.

BRIEF SUMMARY OF THE INVENTION

The present invention relates to cleaning compositions that are suitable for cleaning a range of surfaces and to methods of use of such compositions. The cleaning compositions contain a probiotic component which adds a layer of probiotic bacteria to the surface being cleaned. These probiotic bacteria quickly colonise and consequently there is no space for pathogenic bacteria to grow and colonise the cleaned surface. If a pathogenic bacterium were to land on the cleaned surface, or remain behind on the surface after cleaning, this pathogenic bacterium would be out-competed by the layer of probiotic bacteria added to the surface by the cleaning composition claimed herein. The cleaning compositions are used to clean a range of surfaces in the domestic, public or industrial environment. The cleaning compositions are used to clean surfaces, for example, in domestic bathrooms and kitchens and hospital environments.

According to a first aspect of the present invention, there is provided anaqueous composition comprising: at least one strain of Class 1 *Bacillus* bacterial spores, selected from *Bacillus Cirulans, Bacillus Megaterium, Bacillus Lichenforms, Bacillus Pumilus, Bacillus Sphaericus, Bacillus Subtilis* sub species 10144 and *Bacillus Subtilis* sub species 8646, a terpene, and one or more surfactants.

The terpene is preferably d-limonene. The aqueous composition may further comprise citric acid.

Preferably, at least one strain of Class 1 *Bacillus* bacterial spores is selected from *Bacillus Cirulans, Bacillus Megaterium* and *Bacillus Sphaericus*.

Preferably, the aqueous composition is in the form of a concentrate.

According to a second aspect of the present invention, there is provided a method of cleaning surfaces, the method comprising deploying an aqueous composition comprising at least one strain of Class 1 *Bacillus* bacterial spores, selected from *Bacillus Cirulans, Bacillus Megaterium, Bacillus Lichenforms, Bacillus Pumilus, Bacillus Sphaericus, Bacillus Subtilis* sub species 10144 and *Bacillus Subtilis* sub species 8646, a terpene and one or more surfactants to the surface. The surface may be either a hard surface or a soft surface.

BRIEF DESCRIPTION OF THE DRAWINGS

FIG. 4 is a table displaying results for each treatment and time point as carried out in the Example section of the application.

FIG. 5 is a table displaying results for the effectiveness of the present cleaning composition in accordance with the Example section of the application.

DETAILED DESCRIPTION OF THE PREFERRED EMBODIMENTS

Figure 1:
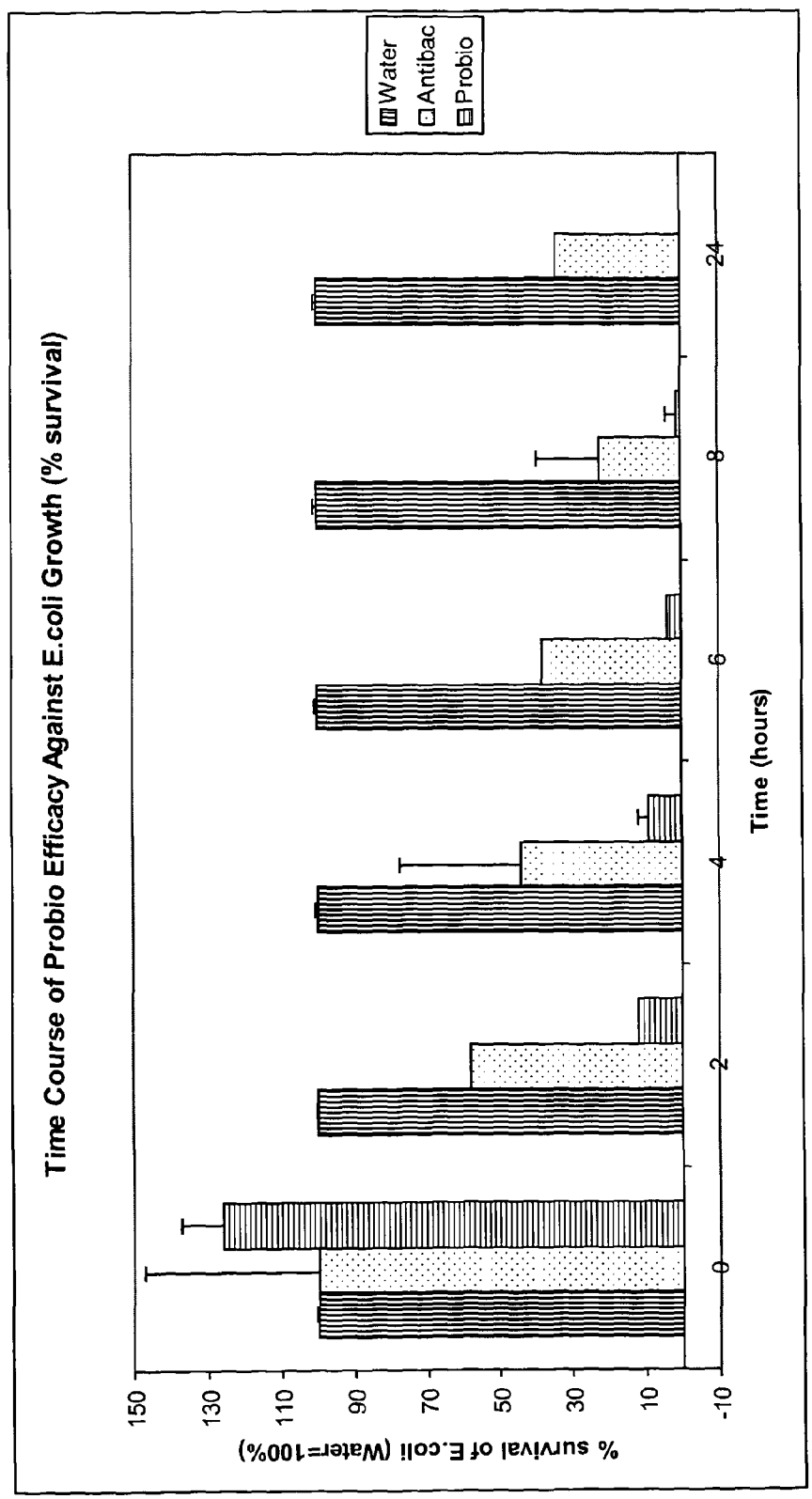
FIG. 1 is a graph depicting results from the Example section of the application.

The present invention provides an aqueous composition comprising at least one strain of Class 1 *Bacillus* bacterial spores, a cleaning compound, and one or more surfactants. The cleaning compound is preferably d-limonene.

The aqueous composition may further comprise citric acid. Anhydrous citric acid may be used in the aqueous composition. The anhydrous citric acid may be present in an amount from 0.1% to 2% by total weight. The inclusion of citric acid aids in the reduction of limescale. Citric acid may be used in cleaning compositions when used as, for example, a multi-surface cleaner, bathroom cleaner, toilet cleaner and barbecue cleaner.

The inventors have found that bacterial cultures derived from strains of the genus *Bacillus* have good efficacy in the cleaning composition. At least one strain of *Bacillus* bacteria is selected from *Bacillus Cirulans, Bacillus Megaterium, Bacillus Lichenforms, Bacillus Pumilus, Bacillus Sphaericus, Bacillus Subtilis* sub species 10144 and *Bacillus Subtilis* sub species 8646. Each of these strains, *Bacillus Cirulans, Bacillus Megaterium, Bacillus Lichenforms, Bacillus Pumilus, Bacillus Sphaericus, Bacillus Subtilis* sub species 10144 and *Bacillus Subtilis* sub species 8646, is deposited with the National Collection of Industrial, food and Marine Bacteria (NCIMB Ltd). The Registered Office of NCIMB Ltd is Ferguson Building, Craibstone Estate, Bucksburn, Aberdeen, AB21 9YA. Each of the bacterial strains used is therefore from a commercial bacterial culture collection and is fully traceable.

*Bacillus Cirulans* was deposited under accession number 7578 by the National Collection of Type Cultures (as NCTC7578); *Bacillus Megaterium* was deposited under accession number 4821 by the National Collection of Type Cultures (as NCTC4821); *Bacillus Lichenforms* was deposited under accession number 1042 and is also known as ATCC14409; *Bacillus Pumilus* was deposited under accession number 1522; *Bacillus Sphaericus* was deposited under accession number 8216; *Bacillus Subtilis* sub species 10144 was deposited under accession number 10144; *Bacillus Subtilis* sub species 8646 was deposited under accession number 8646.

However, preferably at least one strain of *Bacillus* bacteria is selected from *Bacillus Circulans, Bacillus Megaterium* and *Bacillus Sphaericus*.

The *Bacillus* bacteria provide the present aqueous composition with a probiotic activity. The *Bacillus* bacteria are known to be probiotic. The standard definition for a probiotic substance is a substance containing live microorganisms that claims to be beneficial to humans and animals, for example, by restoring the balance of microflora in the digestive tract. The presence of at least one strain of *Bacillus* bacteria in the present composition allows a layer of probiotic bacteria to be added to a surface being cleaned. These probiotic *Bacillus* bacteria quickly colonise and consequently there is no space for pathogenic bacteria to grow and colonise the cleaned surface. If a pathogenic bacterium were to land on the cleaned surface, or remain behind on the surface after cleaning, this pathogenic bacterium would be out-competed by the layer of probiotic *Bacillus* bacteria added to the surface by the cleaning composition claimed herein.

The aqueous composition comprises 0.1% to 5% by volume (in ready to use form) of culture media containing Class 1 *Bacillus* bacterial spores. The culture media is present in a concentration wherein the bacterial count is within the range of 100,000 to 100,000,000 per milliliter.

Preferably the aqueous composition comprises 0.2% to 0.5% by volume (in ready to use form) of culture media containing Class 1 *Bacillus* bacterial spores. The culture media is present in a concentration wherein the bacterial count is within the range of 100,000 to 100,000,000 per milliliter.

The composition may be prepared in the form of a concentrate and may be diluted with water prior to use. The composition of the invention may be in solid or liquid form.

The composition may be rehydrated or dissolved in a solvent, including water, before use. The composition may also be in a ready to use composition. The composition may also be used as an active ingredient to be incorporated into other cleaning compositions.

The composition may comprise a solvent. In a preferred embodiment the solvent is water. The composition may also include an organic solvent such as isopropyl alcohol or a glycol ether.

In one embodiment, the composition is a cleaning composition in the form of a spray. In an alternative embodiment, the composition is a cleaning composition in the form of an aerosol. In an alternative embodiment, the cleaning composition is in the form of a liquid. In a further embodiment, the cleaning composition is in the form of a powder. In a yet further embodiment, the cleaning composition is provided on wipe cleaners.

The cleaning compound is preferably a non-toxic ingredient. The cleaning compound may be a dirt and stain remover or a degreasing agent. In a preferred embodiment the cleaning compound is in the form of terpenes, and most preferably a monoterpene. The preferred monoterpene is d-limonene.

The d-limonene, also known as orange terpene, is the chemical that is recovered from pressed orange or citrus peels. d-Limonene (or orange terpene) is extremely effective in cleaning in cleaning products for use in industrial and household environments.

Preferably, the aqueous cleaning composition comprises 0.1% to 25% of d-limonene by weight when in the ready to use form of composition. In a preferred embodiment, the aqueous cleaning composition comprises 0.2% to 10% of d-limonene by weight when in the ready to use form of composition.

The d-limonene may be used as a concentrate in a blend comprising anionic and non-ionic surfactants. In a preferred embodiment, the d-limonene may be used as a concentrate in a blend of trisodium salt, hydroxyethylenediaminetriacetate and monomethylethers of dipropylene glycol.

The claimed aqueous composition also comprises one or more surfactants. Suitable surfactants are nonionic surfactants, anionic surfactants, cationic surfactants, amphoteric surfactants, zwitterionic surfactants, and mixtures thereof. The surfactants used should cause minimal harm to the Class 1 *Bacillus* bacteria.

The aqueous composition of the claimed invention may comprise 0.1% to 35% by weight of surfactant when in the ready to use form of composition. In one embodiment, the composition for use as a multi-surface and bathroom cleaner may comprise 0.1% to 3% by weight surfactant when in the ready to use composition. In an embodiment, the composition for use as a toilet cleaner may comprise 5% to 10% by weight surfactant when in the ready to use composition. In an embodiment, the composition for use as a washing-up liquid may comprise 18% to 30% by weight surfactant when in the ready to use composition.

In a preferred embodiment, the composition comprises a blend of anionic and non-ionic surfactants. In a preferred embodiment, the anionic surfactants may be an amine salt of alkyl benzene sulphonic acid and alkyl ether sulphate. In a preferred embodiment, the non-ionic surfactant may be cocamide diethanolamide.

The ratio between anionic surfactant(s) and non-ionic surfactant(s) may in a preferred embodiment be between 60:40 and 30:70 and preferably between 50:50.

In one embodiment of the invention the blend of anionic and non-ionic surfactants in the aqueous cleaning composition is formulated as follows: 25-50% concentration amine salt of alkyl benzene sulphonic acid, 5-10% alkyl ether sulphate and 25-50% concentration cocamide diethanolamide.

However, the anionic surfactant(s) may be any anionic surfactants well known to those skilled in the art. The anionic surfactants may be water soluble anionic surfactants and/or water insoluble anionic surfactants. Preferred anionic surfactants include sulphate and sulphonic acid metal salts and alkyl ether sulphates. More preferably, the anionic surfactants include alkyl benzene sulphonic acid and salts. These salts are commonly known as alkyl benzene sulphonates. Said salts preferably have a hydrocarbyl group of from 5 to 20, in one embodiment from 7-18 carbon atoms and in a further embodiment from 8-14 carbon atoms. The metal ion in these metal salts is preferably sodium and potassium with sodium being more preferred.

The salt of the alkyl benzene sulphonic acid is preferably an amine salt. A wide variety of amines may be used to form the salt of the alkyl benzene sulphonic acid. Amines which can be used include the primary, secondary and tertiary alkylamines or alkanolamines, aromatic amines, cyclic amines and heterocyclic compounds containing N as heteroatom. Particularly suitable amines, however, are methylamine and ethylamine and especially suitable salts are the methylamine salts of dodecyl benzene sulphonic acid and tridecyl benzene sulphonic acid, and the triethylamine salts of undecyl benzene sulphonic acid and dodecyl benzene sulphonic acid.

Alkyl ether sulphates are also preferred anionic surfactants. Particularly suitable alkyl ether sulphates are sodium salts, such as sodium laureth-2 sulphate and sodium laureth-3 sulphate.

Further examples of suitable water soluble anionic surfactants include those selected from the group consisting of alkyl amido ether sulphates, alkyl aryl polyether sulphates, alkyl aryl sulphates, monoglyceride sulphates, alkyl sulphonates, benzene sulphonates, toluene sulphonates, xylene sulphonates, alkyl benzene sulphonates, alkyl diphenyloxide sulphonates, paraffin sulphonates, lignin sulphonates, alkyl sulfosuccinates, ethoxylated sulfosuccinates, alkyl ether sulfosuccinates, alkylamide sulfosuccinates, alkyl sulfoacetates, alkyl phosphates, phosphate ester, alkyl ether phosphates, acyl sarconsinates, acyl isethionates and alkyl carboxylates.

Examples of suitable water soluble anionic surfactants include sodium lauryl sulphate, sodium dodecyl benzene sulfonate, disodium octyl sulfosuccinate, sodium stearate and sodium lauroyl sarcoside.

Examples of suitable anionic surfactants may also include alkyl sulphates, alpha olefin sulphonates, fatty acid ester sulphates, and phosphate esters.

Examples of suitable non-ionic surfactants include those based on alkyl poly(ethylene oxide); alkylphenol poly(ethylene oxide); copolymers of poly(ethylene oxide); and poly (propylene oxide) (commercially called Poloxamers or Poloxamines); alkyl polyglucosides, including for example octylglucoside, decyl maltoside; fatty alcohols such as for example cetyl alcohol and oleyl alcohol, cocamide monoethanolamide, cocamide diethanolamide; polysorbates such as Tween 20 and Tween 80; dodecyl dimethylamine oxides and alcohol ethoxylates. A preferred blend of anionic and non-ionic surfactants comprises an amine salt of alkyl benzene sulphonic acid, alkyl ether sulphate and cocamide diethanolamide (also known as coconut diethanolamide). Such a blend can be commercially obtained from a range of suppliers, for example as CAFLON® DW95 from Univar Ltd. Preferably the blend comprises 25-50% of an amine salt of alkyl benzene sulphonic acid, 5-10% alkyl ether sulphate and 25-50% of cocamide diethanolamide.

The present invention also provides a method of cleaning surfaces, which method comprises deploying an aqueous composition according to claim 1 to the surface.

The present invention provides a method for cleaning a surface comprising contacting the surface in need of cleaning with the foregoing aqueous composition in an amount effective for providing cleaning treatment. Suitable surfaces include without limitation, hard surfaces such as metal, glass, ceramic, concrete, plastic, wood and other similar surfaces. More particularly these hard surfaces may include dirty dishes, plates and pans and any other kitchen utensil to be cleaned, painted woodwork and panels, kitchen work benches, tiled walls, wash bowls, toilets, bathtubs, linoleum and washable wallpaper. The surfaces are not limited to hard surfaces and may also include soft surfaces such as fabric surfaces, carpets, upholstery, clothing and other fabric surfaces. The method of cleaning may be carried out in a variety of environments including domestic, industrial, healthcare, care homes, catering, leisure and public conveniences. The method may comprise using the cleaning composition directly (neat) or first diluting the composition in a sufficient amount of water or other carrier.

For such cleaning purposes, the claimed composition may be formulated so as to be suitable as but not restricted to a toilet cleaner, multi-surface cleaner, bathroom cleaner, washing-up liquid, floor cleaner and barbecue cleaner.

The present invention also provides a cleaning product kit comprising the aqueous composition and a source of water.

The claimed aqueous cleaning composition may also optionally include one or more conventional additives known to be useful in aqueous cleaning compositions. Such additives may include viscosity modification agents; fragrances (natural or synthetically produced); foaming agents; water softening agents; preservatives; stabilizing agents; additional co-surfactants including anionic, cationic, nonionic, amphoteric and zwitterionic surface active agents, especially those useful in providing further detersive effects; additional organic solvents for physical stability purposes; sequestering agents (chelating agents) such as phosphonate chelating agents; amino carboxylate chelating agents (for example, EDTA and metal salts thereof); carboxylate chelating agents; polyfunctionally-substituted aromatic chelating agents and mixtures thereof; and colouring agents.

Such optional constituents should be selected so as to have little or no detrimental effect upon the probiotic behaviour of the Class 1 *Bacillus* bacteria provided by the inventive compositions claimed herein. Such optional ingredients are well known to those of ordinary skill in the art.

The invention is further illustrated and will be further understood with reference to the following examples. These examples are not intended, however, to limit or restrict the scope of the invention in anyway and should not be construed as providing conditions, parameters or values which must be utilized exclusively in order to practice the present invention. Unless otherwise specified, all parts and percents are by weight, and all temperatures are in degrees Centigrade.

Example 1

A culture of *Bacillus* bacteria is grown overnight in 10 milliliters (ml) of a complex nutrient rich media like LB (lysogeny broth) at 35° C. with shaking at 250 revolutions per minute (rpm). Any culture that does not reach a minimal OD600 of 1.0 (OD=optical density) is re-inoculated at a later date and not used.

Example 2

The cleaning composition according to the present invention is prepared as a concentrate by adding to water, the cleaning compound, one or more surfactants, and the culture of *Bacillus Circulans, Bacillus Megaterium* and *Bacillus Sphaericus*. Where required, citric acid is also added. The composition is stirred thoroughly.

Example 3

The *Bacillus* bacterial strain-containing aqueous cleaning composition was tested by comparison studies with an anti-microbial agent and water. The effect on the reduction of *E. coli* bacteria after a specified length of time was examined.

The strain used is from a commercial bacterial culture collection and is fully traceable. The strain used is *Escherichia coli* (*E. coli*): ATCC 25922. *E. coli* was cultured for 18 hours in tryptone soya broth (TSB) at 44° C. prior to use in the experiments.

The present cleaning composition was diluted 1:5 in sterile water. 10 ml was filtered through a cellulose nitrate membrane allowing concentration of the bacterial spores present in the product on the surface of the membrane.

Filtration was repeated on separate membranes with 10 ml of sterile water (control 1) and antibacterial agent diluted 1:5 in sterile water (control 2).

The membranes were then placed on the surface of tryptone soya agar (TSA), a standard nutrient rich bacterial growth medium, and the plates and incubated for 18 hours at 22° C.

Stationary phase *E. coli* cultures were diluted to $10^{-4}$ in maximum recovery diluent (MRD), an isotonic protective medium. One ml of diluent was then added directly to the surface of the membrane (approximately 1000 cells/membrane). Membranes were incubated at 22° C. for the following times: 0 hours, 2 hours, 4 hours, 6 hours, 8 hours and 24 hours. The time course was performed using membranes exposed to each of the experimental conditions i.e: sterile water (control 1), antibacterial agent (control 2) and the present cleaning composition, to enable accurate comparison of the growth of *E. coli* in relation to each treatment.

After the appropriate incubation time (for example, 2 hours) the membranes were removed into 10 ml MRD. After vortexing for 10 sec (to release the bacteria from the membrane into solution), 1 ml of MRD was taken and added to a sterile petri dish. Fifteen ml of molten Tryptone Bile X-Glucuronide (TBX) Agar was subsequently added to the sample and mixed thoroughly. After allowing the plates to set they were incubated at 44° C. for 18 hours. TBX medium contains bile salts which inhibit the growth of other gram positive bacteria. The medium also contains XD-glucuronide which detects glucuronidase activity, an enzyme specific to *E. coli*, causing *E. coli* colonies to turn blue/green. This enables easy identification of *E. coli* colonies.

After 18 hours the number of viable *E. coli* cells on each plate was determined by colony counting.

All experiments were performed in duplicate.

Results are displayed graphically in two different format.

FIG. 1 shows the number of *E. coli* cells expressed as a percentage of water filtered membrane (control 1).

Figure 2:
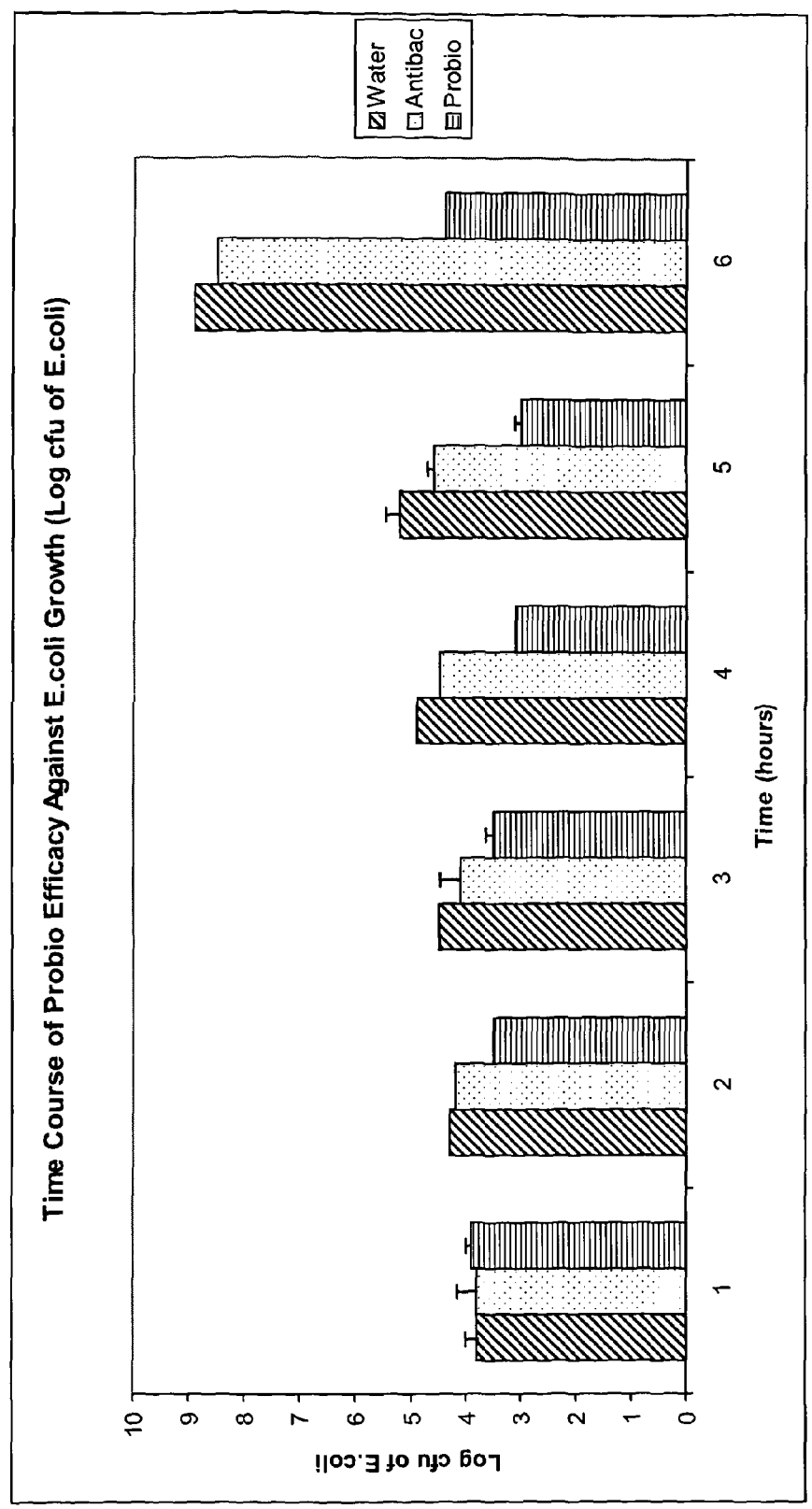
FIG. 2 is a further graph depicting results from the Example section of the application.

FIG. 2 shows the log the total number of viable *E. coli* cells (cfu=colony forming units).

NOTE: Error bars are calculated as the standard deviation of the mean. Results are shown as averages of the duplicate experiment.

Figure 3:
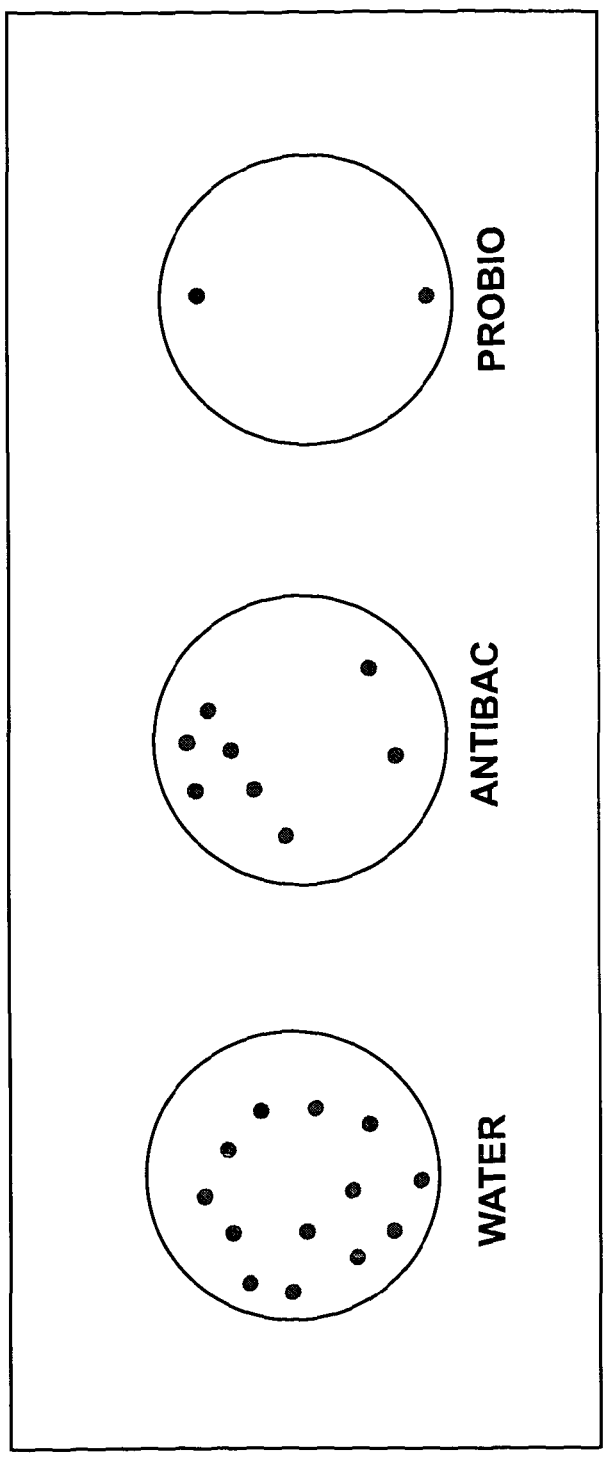
FIG. 3 is a representation of bacterial colony growth from the Example section of the application.

The image shown in FIG. 3 is a representation of 3 TBX plates (representing each of the different membrane treatments) from the 4 hour incubation time point. The small grey circles represent colonies on the plates which are viable *E. coli* cells.

This experiment shows that in the water control membranes, the number of *E. coli* cells multiplies significantly over time (approximately 10,000 times), due to the nutrient rich environment supplied by the tryptone soya agar.

In the antibacterial agent filtered membranes, the bacteria also grow, however at a reduced rate (approximately 50% less) when compared to the water control membrane. This effect is probably due to the reduction in viable numbers of *E. coli* cells in the first instance (ie over the first 2 hours).

In contrast, the rate of *E. coli* growth is considerably reduced on membranes which have been treated with the probiotic. This effect is most drastic after 24 hours (approximately 1000 times less *E. coli* cells when compared to the water control). This suggests that *E. coli* growth is restricted due to competition with the probiotic organisms for nutrients.

The overall results for each treatment and time point indicating the effectiveness of the probiotic as an inhibitor of *E. coli* growth of over time are shown in the table of FIG. 4. The table in FIG. 5 indicates how effective the present cleaning composition is in inhibiting the growth of *E. coli* versus antibacterial agent over time.

Example 4

The strain used is from a commercial bacterial culture collection and is fully traceable. The strain used is *Escherichia coli* (*E. coli*): ATCC 25922. *E. coli* was cultured overnight for 18 hours in Tryptone soya broth (TSB) at 44° C. to obtain a stationary phase culture.

Stationary phase *E. coli* ($10^7$ cfu/ml) was spread onto the surface of tryptone soya agar (TSA) plates. The plates were incubated at 44° C. for 4 hours to enable a preliminary 'bacterial lawn' of *E. coli* to develop. A plug of TSA agar was removed from each plate. The plugs were filled with 0.5 ml of the following:

i) 3× plugs filled with molten TSA agar/0.2% Trigene 1:1 ratio (positive biocide control).
ii) 3× plugs filled with molten TSA agar/probiotic *Bacillus* 1:1 ratio.
iii) 3× plugs filled with molten TSA/Aggies probiotic bio toilet cleaner 1:1 ratio.

The plugs were left to solidify and the plates were then incubated at 30° C. for 24 hours. After 24 hours plates were examined for the presence of 'halos'.

Figure 6:
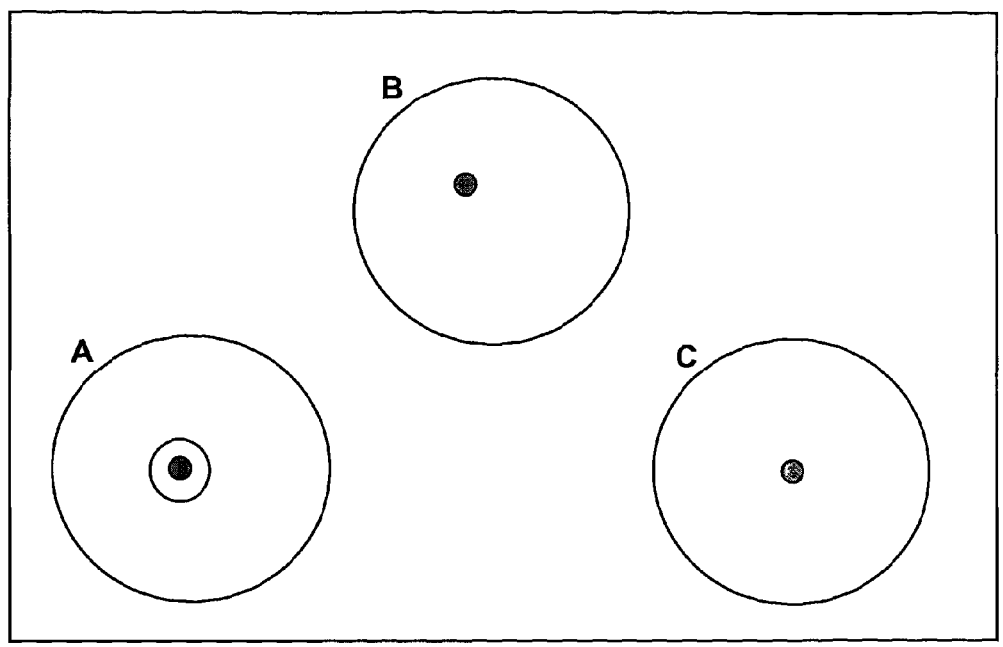
FIG. 6 is a representation of a Halo test as carried out in accordance with the Example section of the application.

The results of the plates are displayed in FIG. 6.

Image A: Halo test performed with 0.2% Trigene (positive biocidal control). Trigene resulted in a 'halo' surrounding the plug of approximately 3 millimeters (mm) in width. This demonstrates that Trigene has killed *E. coli* and thus exhibits biocidal properties.

Image B: Halo test performed with probiotic *Bacillus* strains. The plug composed of probiotic *Bacillus* strains is not surrounded by a halo. This suggests the *Bacillus* strains have not killed *E. coli* and thus do not possess biocidal activity.

Image C: Halo test performed with the claimed composition for use as a probiotic toilet cleaner. The plug composed of the claimed composition for use as a probiotic toilet cleaner is not surrounded by a halo. This suggests the toilet cleaner has not killed *E. coli* and thus does not possess biocidal activity. This 'halo test' methodology suggests that neither the claimed composition for use as a probiotic toilet cleaner nor probiotic *Bacillus* strains exhibit biocidal properties when compared with a known biocidal agent.

The invention claimed is:

1. An aqueous composition comprising:
   a) at least one strain of Class 1 *Bacillus* bacterial spores, selected from *Bacillus Cirulans, Bacillus Megaterium, Bacillus Licheniformis, Bacillus Pumilus, Bacillus Sphaericus, Bacillus Subtilis* sub species 10144 and *Bacillus Subtilis* sub species 8646;
   b) a terpene;
   c) one or more surfactants; and
   d) citric acid.

2. An aqueous composition according to claim 1, wherein the terpene is d-limonene.

3. An aqueous composition according to claim 1, wherein the at least one strain of *Bacillus* bacterial spores is selected from *Bacillus Cirulans, Bacillus Megaterium* and *Bacillus Sphaericus*.

4. An aqueous composition according to claim 1, comprising 0.1% to 5% by volume of Class 1 *Bacillus* bacterial spores, wherein the bacterial count in the culture media lies within the range 100,000 to 100,000,000 per milliliter.

5. An aqueous composition according to claim 4, comprising 0.2% to 0.5% by volume of Class 1 *Bacillus* bacterial spores, wherein the bacterial count in the culture media lies within the range 100,000 to 100,000,000 per milliliter.

6. An aqueous composition according to claim 1 in the form of a concentrate.

7. An aqueous composition according to claim 1 comprising 0.1% to 25% by weight of terpene.

8. An aqueous composition according to claim 7 comprising 0.2% to 10% by weight of terpene.

9. An aqueous composition according to claim 1 wherein the surfactant comprises a blend of anionic and non-ionic surfactants.

10. An aqueous composition according to claim 9, wherein the anionic surfactant is an amine salt of alkyl benzene sulphonic acid and alkyl ether sulphate and the non-ionic surfactant is cocamide diethanolamide.

11. An aqueous composition according to claim 1 comprising 0.1% to 35% by weight of surfactant.

12. An aqueous composition according to claim 11 comprising less than 25% by weight of surfactant.

13. A method of cleaning surfaces, which method comprises deploying an aqueous composition comprising at least one strain of Class 1 *Bacillus* bacterial spores, selected from *Bacillus Cirulans, Bacillus Megaterium, Bacillus Licheniformis, Bacillus Pumilus, Bacillus Sphaericus, Bacillus Subtilis* sub species 10144 and *Bacillus Subtilis* sub species 8646, a terpene, one or more surfactants, and citric acid to a surface.

14. A method according to claim 13, wherein the terpene is d-limonene.

15. A method according to claim 13, wherein the at least one strain of *Bacillus* bacterial spores is selected from *Bacillus Cirulans, Bacillus Megaterium* and *Bacillus Sphaericus*.

16. A method as claimed in claim 13, wherein said surface is a hard surface or a soft surface.

17. A method as claimed in claim 13, wherein the aqueous composition is used directly (neat) or by first diluting the composition in a sufficient amount of water or other carrier.

18. A cleaning product kit comprising a composition according to claim 1 and a source of water.

* * * * *